United States Patent [19]

Maier et al.

[11] Patent Number: 4,569,917

[45] Date of Patent: Feb. 11, 1986

[54] METHOD FOR THE DIRECT DETERMINATION OF THE LIPID CONTENT OF BLOOD BETA-LIPOPROTEINS

[75] Inventors: Josef Maier; Manfred Gloger, both of Weilheim; Brigitte Draeger, Tutzing, all of Fed. Rep. of Germany

[73] Assignee: Boehringer Mannheim GmbH, Mannheim, Fed. Rep. of Germany

[21] Appl. No.: 240,720

[22] Filed: Mar. 5, 1981

[30] Foreign Application Priority Data

Mar. 8, 1980 [DE] Fed. Rep. of Germany ....... 3009037

[51] Int. Cl.$^4$ .............................................. G01N 33/92
[52] U.S. Cl. ..................................... 436/71; 210/635; 260/112 R; 436/178
[58] Field of Search ...................... 23/230 B, 902, 909; 260/112 B, 112 R; 210/198.2, 635; 521/30; 252/408; 436/71, 178

[56] References Cited

U.S. PATENT DOCUMENTS

| | | | |
|---|---|---|---|
| 3,573,277 | 3/1971 | Grant | 521/30 X |
| 3,664,994 | 5/1972 | Perper | 260/112 B |
| 3,983,299 | 9/1976 | Regnier | 210/198.2 X |
| 4,029,583 | 6/1977 | Chang et al. | 210/198.2 X |
| 4,096,136 | 6/1978 | Ayers et al. | 260/112 B |
| 4,100,149 | 7/1978 | Meiller et al. | 260/112 R |
| 4,178,439 | 12/1979 | Ayers et al. | 536/1 X |

OTHER PUBLICATIONS

Rubenstein et al., Canadian Journal of Biochemistry, 54, 1023–1028, 1976.

Heuck et al., Clinical Chemistry, vol. 23, No. 3, 1977, pp. 536–540; and No. 9; pp. 1756–1759.

*Primary Examiner*—Arnold Turk
*Attorney, Agent, or Firm*—Felfe & Lynch

[57] ABSTRACT

Method of direct determination of beta-lipoproteins in a blood sample containing pre-beta-lipoprotein, (VLDL) alpha-lipoprotein (HDL), and beta-lipoprotein (LDL), comprising mixing the blood plasma or serum of the blood sample with a solid, water-insoluble anion exchanger operable to retain the pre-beta-lipoprotein (VLDL) and the alpha-lipoprotein (HDL) to remove them from solution, separating the blood plasma or serum from the anion exchanger and thereafter determining the amount of beta-lipoprotein (LDL) remaining in solution.

19 Claims, No Drawings

METHOD FOR THE DIRECT DETERMINATION OF THE LIPID CONTENT OF BLOOD BETA-LIPOPROTEINS

This invention relates to a composition and method for the direct determination of the lipid content of the beta-lipoproteins of the blood. More specifically, the present invention provides such a method involving the selective separation of the lipoprotein fractions from blood plasma or serum, the plasma or serum being mixed with polycations and the complexes formed from the polycations and the lipoproteins being removed fractionally from the solution.

Such a process is known from Federal Republic of Germany Patent Specification No. 26 00 664, in which weak polycations present in solution, preferably in the form of a 40% polyethyleneimine (PEI) solution, are added to the serum, soluble lipoprotein-PEI complexes thereby being formed. These soluble lipoprotein-PEI complexes are selectively removed from the solution by shaking the serum, previously mixed with polyethyleneimine solution, with a weakly acidic cation exchanger, for example a methacrylic acid-divinylbenzene copolymer in the H-form, and decanting off the supernatant. A selective separation of the three lipoprotein fractions, namely, the $\beta$-lipoproteins (low density liproproteins=LDL), on the one hand, and the pre-$\beta$-lipoproteins (very low density liproproteins=VLDL) and $\alpha$-lipoproteins (high density lipoproteins=HDL), on the other hand, is achieved due to the surprising fact that the soluble complexes of $\beta$-liproprotein and PEI remain free in the solution, whereas the soluble complexes of pre-$\beta$-lipoprotein and PEI and the soluble complexes of $\alpha$-lipoprotein and PEI are adsorbed on the weakly acid cation exchanger. The supernatant is decanted off and the lipid content of the decanted off supernatant is then determined by known processes: the cholesterol content of the LDL fraction contained in the decanted off supernatant, which corresponds to the content of $\beta$-cholesterol in the serum, is determined chemically by the Liebermann-Burchard process or enzymatically.

This process known from Federal Republic of Germany Patent Specification No. 26 00 664 admittedly gives reproducible measurement results which agree, within the limits of error of $\pm 10\%$, with the reference values of the ultracentrifuge method (separation of the three lipoprotein fractions according to density gradients in an ultracentrifuge; cf. Med. Labor., 30(12), pp. 294–301/1977) but its clinical usefulness is limited by the fact that it is a comparatively time-consuming and slow process which requires the use of trained personnel. Furthermore, the addition of adjuvant ion exchangers, in addition to the polycations needed for the complex formation, involves the danger of introducing impurities, as well as the danger that a part of the LDL fraction present in the supernatant is lost in the automatically necessary decanting, washing out and filtering. For these reasons, this known process is not very suitable as a standardized routine process without special laboratory expense which can also be carried out quickly and certainly by untrained personnel.

Federal Republic of Germany Patent Specification No. 27 08 912 describes another process for the selective separation of lipoproteins from blood plasma or serum in which the plasma or serum is first mixed with bivalent cations, for example magnesium, calcium or manganese ions, and subsequently with a cation exchanger which, as fixed ions, contains sulphate ions and, as opposed ions, also contains bivalent cations, such as magnesium, calcium or manganese. The skeletal framework of the cation exchanger consists of a cross-linked carbohydrate, a cross-linked polysaccharide or cross-linked cellulose which can possibly be modified with lower hydroxyalkyl radicals. In contradistinction to the initially mentioned process, this process can admittedly be employed quickly, reproducibly and economically as a column process but has the disadvantage that the LDL and VLDL lipoprotein fractions are always adsorbed together on the cation exchanger, whereas the $\alpha$-lipoproteins remain in the eluate of the first column. The determination of the lipid content of the $\alpha$-lipoproteins, i.e. of the LDL fraction alone, is not possible with this process.

The problem with which the present invention is concerned is to provide a process of the initially mentioned kind which can be employed quickly, reproducibly and economically as a column process, without suffering from the above-mentioned disadvantages, as well as a diagnostic agent for carrying out this process.

Thus, according to the present invention, there is provided a process for the direct determination of the lipid content of the $\beta$-lipoproteins of blood by selective separation of the lipoprotein fractions from blood plasma or serum, the plasma or serum being mixed with polycations and the complexes formed from the polycations and the lipoproteins being fractionally removed from the solution, wherein the pre-$\beta$-liproproteins (VLDL) and $\alpha$-lipoproteins (HDL) are separated by mixing the plasma or serum with a solid, water-insoluble anion exchanger and the lipid content of the $\beta$-lipoproteins (LDL) remaining in solution is measured in known manner.

The process according to the present invention enables the body fluid to be investigated without the addition of an aqueous reagent solution and without having to stir a solid, powdered or granulated adjuvant ion exchanger into the body fluid so that all the difficulties which arose in the case of the previously known processes in connection with the separation of the adjuvant ion exchanger or the mixing of the fluid to be investigated with foreign solutions are avoided. In the case of the process according to the present invention, the functions of the polyethyleneimine previously added in the form of an aqueous solution, namely the complex formation with the lipoproteins, and the functions of the previously separately added adjuvant ion exchanger, namely the selective adsorption of the lipoprotein-PEI complexes, are combined into a single step so that it is not necessary either to prepare any kind of reagent solutions and to purify and separate or to decant, filter or purify the eluate. The solid anion exchanger used according to the present invention only needs to be packed into a column and the body fluid to be investigated chromatographed in conventional manner, the LDL fraction thereby passing through unhindered, whereas the VLDL and the HDL fractions are adsorbed on the insoluble carrier.

Advantageous further developments of the process according to the present invention are described in the following examples.

The use of basic anion exchangers which contain quaternary ammonium groups as fixed ions, especially the use of cross-linked PEI and of dextrans containing quaternary ammonium groups, is advantageous. Diethyl-2-hydroxypropylammonium groups are especially preferred as fixed ions in the case of dextrans. Furthermore, the use of PEI cross-linked with bifunctional epoxide compounds, preferably epichlorohydrin, or with dialdehydes which are derived from dicarboxylic acids containing 3 to 6 carbon atoms, preferably glutardialdehyde, is especially advantageous. The cross-linking of the PEI can be carried out, for example, by the processes described in U.S. Pat. No. 3,796,634 and in Federal Republic of Germany Patent Specifications Nos. 1,168,078 and 1,056,825, epichlorohydrin thereby being preferably used in an amount of from 2.5 to 3.5 ml. for the cross-linking of 21.6 ml. (20 g.) amounts of a 50% PEI solution.

When using water-insoluble, cross-linked PEI for the separation of the VLDL and HDL fractions, depending upon the nature and origin of the sample to be investigated, about 5 to 10% of the proportion of HDL in the serum or plasma passes in the throughflow into the LDL fraction. However, this proportion is so small that it can only be detected electrophoretically.

However, it has been found that even the 5 to 10% proportion of HDL in the eluate can be avoided when cross-linking of the PEI is carried out in the presence of porous ceramic materials or of porous glasses with a definite pore, size, i.e. so-called "controlled pore glasses". Examples of porous ceramic materials which can be used for this purpose include calcined clay, kieselguhr and diatomaceous earth, as well as commercially available products based on these materials but mixed with a large variety of polymers, whereas, in the case of the CPG glasses, those with an average pore diameter of 175 to 250 Å have proved to give optimum results.

Furthermore, the use of PEI cross-linked in the presence of ceramic materials or of CPG glasses has the advantage that a disturbing swelling behavior of PEI gels with a low degree of cross-linking, which may occur under certain circumstances, can be avoided with certainty.

Especially in the case of turbid sera in the process according to the present invention, it may also happen that a small proportion of the VLDL fraction passes in the throughflow into the LDL. However, it has been found that this can be avoided by modifying the cross-linked polyethyleneimine employed with hydrophobic residues, especially hydrophobic amines, when carrying out the cross-linking. Examples of hydrophobic amines which can be used include primary, straight-chained or branched alkylamines containing 3 to 12 carbon atoms, such as propylamine, n-butylamine, tert.-butylamine, hexylamine, dodecylamine, N-hydroxymethylethyleneimine, 3-amino-2,2-dimethylpropan-1-ol and N,N-2-tetramethylpropane-1,3-diamine. These amines are added as co-monomers when carrying out the cross-linking of the PEI with bifunctional epoxide compounds or with dialdehydes.

Generally speaking, the degree of separation of the individual lipoprotein fractions on the column depends not only upon the ionic strength of the solution but also upon the pH value and the degree of cross-linking of the PEI matrix, the binding power of the PEI matrix for lipoproteins decreasing with an increasing degree of cross-linking.

Furthermore, it has been found that for the separation of the pre-$\beta$-lipoproteins and $\alpha$-lipoproteins from the plasma or serum, those anion exchangers may be especially advantageously used in the polymeric matrices of which are incorporated dextrans and preferably those with an average molecular weight of 20,000 to 800,000. The dextrans are thereby advantageously added during the cross-linking of the anion exchanger, especially of the polyethyleneimine, with bifunctional epoxide compounds or with dialdehydes, to the still not cross-linked anion exchanger, so that the dextran units are also incorporated into the polymeric matrix during the cross-linking.

According to a preferred embodiment of the process of the present invention, the VLDL and HDL fractions are separated from the LDL fractions by applying plasma or serum to a column packed with the solid, optionally cross-linked anion exchanger or with the finely-divided, porous carrier material coated therewith and chromatographed with a buffer solution with a pH of from 6.5 to 7.5, the LDL, VLDL and HDL being selectively eluted. The buffer solution used for the elution of the LDL may be, for example, a sodium-chloride-imidazole-hydrochloric acid buffer. Furthermore, the sodium chloride concentration of the buffer may, after elution of the LDL, be increased stepwise until the VLDL can be detected in the eluate, which is then completely eluted at a constant sodium chloride concentration and thereafter the HDL is eluted with a pure sodium chloride solution.

The present invention also provides a diagnostic agent for carrying out the process according to the present invention which contains one of the anion exchangers used in the process according to the present invention.

The diagnostic agent in the form of a test pack or test combination preferably contains all of the necessary reagents, each of which are packed separately in an amount sufficient for one determination or for a series of determinations. The test pack can also contain a test column. For example, the diagnostic agent according to the present invention can comprise:

(a) a test column of transparent or translucent material;

(b) an amount, sufficient for packing a test column, of an anion exchanger used according to the process of the present invention;

(c) a separately packed and appropriate buffer solution, pH 6.5 to 7.5, for the elution of the lipoprotein fractions; and (d) a pure sodium chloride solution which is also separately packed.

The preparation of anion exchangers which may be used according to the present invention is described, by way of example, in the following:

Anion exchanger 1

PEI-epichlorohydrin-"Chromosorb"

20 g. 50% Polyethyleneimine solution (G 35, BASF) are dissolved in 38 ml. 0.5M aqueous sodium hydroxide solution and cross-linked with 2.5 ml. epichlorohydrin. The batch is vigorously stirred for 15 minutes and used for coating by stirring into about 50 g. "Chromosorb" (Registered Trade Mark of the Johns-Manville International Corporation, New York, U.S.; commercially available carrier material based upon diatomaceous earth) and subsequently heating for 3 hours at 60° C. The anion exchanger thus obtained is comminuted in a test sieve (mesh size 0.5 mm.), freed from very fine particles, adequately washed and pre-equilibrated with 0.33M aqueous sodium chloride solution-0.05M imidazolehydrochloric acid buffer (pH 7.2).

Anion exchanger 2

PEI-epichlorohydrin comonomer-"Chromosorb"

Cross-linking of the PEI with epichlorohydrin is carried out in the manner described for the preparation of anion exchanger 1 but in the presence of the comonomers mentioned in the following, using the following components:

10 g. PEI (50% solution)
20 ml. 0.5M aqueous sodium hydroxide solution
5 ml. dioxan, as well as either
0.2 g. butylamine or
0.2 g. propylamine or
0.2 g. hexylamine or
0.2 g. dodecylamine or
0.5 g. N-hydroxymethyl-ethyleneimine or
2 g. 3-amino-2,2-dimethylpropan-1-ol (BASF) or
1.5 g. N,N-2-tetramethylpropane-1,3-diamine.

Working up is carried out as in the case of the preparation of anion exchanger 1.

Anion exchanger 3

PEI-glutardialdehyde-CPG glass or "Spherosil"

5 g. CPG glass with an average pore diameter of 250 Å (producer: Electro-Nucleonics) are wetted with a glutardialdehyde solution and, while stirring gently, reacted with a 10% PEI solution (pH 8.0). After 30 minutes, the reaction mixture is decanted and the coated glass particles are thoroughly washed with 0.1N hydrochloric acid, 0.1N aqueous sodium hydroxide solution and water.

Anion exchanger 4

PEI-epichlorohydrin-CPG glass

A mixture of 20 g. 50% PEI-G 35 (BASF), 45 ml. 0.5M sodium hydroxide solution and 2.5 ml. epichlorohydrin is vigorously stirred for 2 hours at ambient temperature. 70 g. CPG glass with an average pore diameter of 177 Å (producer: Electro-Nucleonics) are wetted with this solution and kept for 2 hours at 70° C. The coated glass particles are packed into a column and washed with 2 liters 1M hydrochloric acid, 5 liters 0.5M phosphate buffer (pH 7.4) and subsequently with the same amount of double distilled water. For the separation of the lipoproteins, the anion exchanger is pre-equilibrated with 0.25M aqueous sodium chloride solution-0.05M imidazole-hydrochloric acid buffer (pH 7.2) or with 0.42M aqueous potassium chloride solution.

Anion exchanger 5

PEI/dextran-epichlorohydrin-CPG glass

A mixture of 20 g. 50% PEI-G 35 (BASF), 45 ml. 0.5M aqueous sodium hydroxide solution, 1 g. dextran T500 (producer: Pharmacia, average molecular weight 500,000) and 2.5 ml. epichlorohydrin is vigorously stirred for 2 hours at ambient temperature. 56 g. CPG glass with an average pore diameter of 200 Å are wetted with this solution and kept for 2 hours at 70° C. The coated glass particles are washed and pre-equilibrated in the manner described in the case of anion exchanger 4.

Anion exchanger 6

PEI/dextran-epichlorohydrin-CPG glass

A mixture of 20 g. 50% PEI-G 35 (BASF), 45 ml. 0.5M aqueous sodium hydroxide solution, 1 g. dextran T70 (average molecular weight 70,000) and 2.5 ml. epichlorohydrin is vigorously stirred for 2 hours at ambient temperature. 56 g. CPG glass with an average pore diameter of 200 Å are wetted with this solution and kept for 2 hours at 70° C. The coated glass particles are washed and pre-equilibrated in the above-described manner.

Anion exchanger 7

PEI/dextran-epichlorohydrin-CPG glass

A mixture of 20 g. 50% PEI-G 35 (BASF), 45 ml. 0.5M sodium hydroxide solution, 1 g. dextran T40 (average molecular weight 40,000) and 2.5 ml. epichlorohydrin is vigorously stirred for 2 hours at ambient temperature. 56 g. CPG glass with an average pore diameter of 200 Å are wetted with this solution and kept for 2 hours at 70° C. The coated glass particles are again washed and pre-equilibrated in the above-described manner.

Anion exchanger 8

Dextran gel containing diethyl-2-hydroxypropylammonium groups (QAE-"Sephadex"; producer Pharmacia) is pre-swollen with water and subsequently exhaustively equilibrated with 0.11M hydrochloric acid and subsequently packed into a column.

The following Example is given for the purpose of illustrating the presentn invention:

EXAMPLE

Determination of the lipid content of the $\beta$-lipoproteins of blood 0.05 to 0.15 ml. of a human serum to be investigated are applied to a column (5×100 mm.) which is packed with 2 ml. of one of the above-described anion exchangers 1 to 8 and which has been pre-equilibrated with 0.25M aqueous sodium chloride solution-0.05M imidazole-hydrochloric acid buffer solution (pH 7.2) or with 0.42M aqueous potassium chloride solution. The column is eluted with 4 ml. of this buffer or with 2 ml. 0.11M aqueous sodium chloride solution and the LDL-cholesterol content in the eluate determined by one of the following known analytical methods:

1. lipoprotein electrophoresis (P. Müller et al., Lab. med., 1, 145–148/1977);
2. cholesterol determination, test combination of Boehringer Mannheim GmbH (P. Roschlau et al., Z. Klin. Chem. Klin. Biochem., 12, 403/1974);
3. LDL-cholesterol according to Friedewald (W. Friedewald et al., Clin. Chem., 18, 499/1972).

The content of LDL-cholesterol is estimated by the following formula (Friedewald):

$$C_{LDL} = C_{serum} - \left( C_{HDL} + \frac{TG}{5} \right)$$

in which C is the cholesterol concentration in mg./100 ml. and TG is the concentration of triglycerides in mg./100 ml.

The lipoproteins (VLDL and HDL fractions) adsorbed on the anion exchanger are eluted with aqueous sodium chloride solution and the HDL cholesterol is, after precipitation of the VLDL fraction with phosphotungstic acid or heparin, determined in the supernatant by one of the known methods.

In the following Table 1, there is compared, for various samples, the particular total cholesterol content in the serum, the cholesterol content of the LDL fraction measured according to Friedewald's method and the cholesterol content of the LDL fraction measured according to the method of the present invention, the measurements in each case being in mg./100 ml. It can thereby be seen that the values obtained by the process according to the present invention agree very well with the values determined by Friedewald's method.

TABLE 1

| | | according to the present invention | | |
|---|---|---|---|---|
| | comparison | Chol.$_{LDL}$ (anion exchanger 1) | Chol.$_{LDL}$ (anion exchanger 5) | Chol.$_{LDL}$ (anion exchanger 8) |
| Chol.$_{Serum}$ | Chol.$_{LDL}$ (Friedewald) | | | |
| 156 | 105 | | 100 | |
| 163 | 102 | | | 109 |
| 165 | 101 | | 92 | |
| 176 | 114 | | 106 | |
| 179 | 110 | | 115 | |
| 180 | 115 | 118 | | |
| 183 | 126 | 121 | | |
| 196 | 114 | | | 122 |
| 198 | 131 | 135 | | |
| 205 | 146 | 138 | | |
| 206 | 126 | | 117 | |
| 209 | 129 | 136 | | |
| 215 | 121 | | 136 | |
| 226 | 156 | | | 146 |
| 230 | 168 | 159 | | |
| 245 | 171 | 185 | | |
| 249 | 161 | 163 | | |
| 262 | 181 | | | 173 |
| 271 | 172 | | | 176 |
| 278 | 194 | 210 | | |
| 281 | 198 | 182 | | |
| 285 | 205 | 198 | | |
| 295 | 209 | 203 | | |
| 309 | 211 | 221 | | |
| 315 | 216 | 224 | | |
| 342 | 209 | 219 | | |
| 364 | 245 | 263 | | |

The following Table 2 demonstrates the precision of the process according to the present invention, by giving the variation coefficients and the amount found as a percentage of the amount actually present.

TABLE 2

| n | Chol.$_{Serum}$ (mg/100 ml) | Chol.$_{LDL}$ (mg/100 ml) | VK | amount found as percentage of amount actually present |
|---|---|---|---|---|
| 10 | 182 | 110 | 2.70 | 96 |
| 10 | 168 | 95 | 2.31 | 95 |
| 10 | 172 | 116 | 3.10 | 94 |
| 8 | 275 | 190 | 2.38 | 96 |
| 10 | 320 | 219 | 2.59 | 95 |
| 10 | 195 | 132 | 2.18 | 97 |
| 6 | 218 | 157 | 1.19 | 96 |
| 10 | 361 | 246 | 2.56 | 94 | n = number of measurements
VK = variation coefficient

The following Table 3 gives, for various sera, the total cholesterol content, the cholesterol content of the HDL fraction, the content of triglycerides, the cholesterol content of the LDL fraction determined according to the present invention using the above-described anion exchanger 4 and the cholesterol content of the LDL fraction determined by Friedewald's method, all the values given being expressed in mg./100 ml.

TABLE 3

| Serum No. | Total cholesterol | HDL-Chol. | Triglycerides | LDL-Chol. (with anion exchanger 4 acc. to invention) | LDL-Chol. (acc. to Friedewald's method) |
|---|---|---|---|---|---|
| 1 | 205 | 41 | 150 | 139 | 134 |
| 2 | 248 | 38 | 175 | 169 | 175 |
| 3 | 174 | 45 | 90 | 108 | 111 |
| 4 (turbid) | 285 | 40 | 330 | 179 | 179 |
| 5 (turbid) | 230 | 30 | 360 | 143 | 128 |
| 6 | 291 | 34 | 174 | 209 | 222 |
| 7 | 184 | 44 | 110 | 112 | 118 |
| 8 | 194 | 38 | 130 | 122 | 130 |
| 9 | 180 | 49 | 95 | 104 | 112 |
| 10 (slightly turbid) | 320 | 45 | 410 | 215 | 193 |
| 11 | 215 | 26 | 160 | 149 | 157 |
| 12 | 203 | 52 | 104 | 124 | 130 |

It will be understood that the specification and examples are illustrative but not limitative of the present invention and that other embodiments within the spirit and scope of the invention will suggest themselves to those skilled in the art.

What is claimed is:

1. A method for direct determination of beta-lipoproteins in a blood sample containing pre-beta-lipoprotein, (VLDL) alpha-liproprotein (HDL), and beta-lipoprotein (LDL), comprising mixing the blood plasma or serum of the blood sample with a solid, water-insoluble anion exchanger operable to retain the pre-beta-lipoprotein (VLDL) and the alpha-lipoprotein (HDL) to remove them from solution while allowing the beta-lipoprotein (LDL) to remain in solution, separating the blood plasma or serum from the anion exchanger and thereafter determining the amount of beta-lipoprotein (LDL) remaining in solution.

2. Method as claimed in claim 1 wherein the anion exchanger used is PEI cross-linked with a bifunctional epoxide compound.

3. Method as claimed in claim 2 wherein the bi-functional epoxide compound is epichlorohydrin.

4. Method as claimed in claim 1 wherein the anion exchanger used is PEI cross-linked with a dialdehyde containing 3 to 6 carbon atoms.

5. Method as claimed in claim 4 wherein the dialdehyde is glutaraldehyde.

6. Method as claimed in claim 2 wherein for the separation of the VLDL and HDL fractions, PEI is used wherein said PEI has been cross-linked with a bifunctional epoxide compound or with a dialdehyde in the presence of a hydrophobic amine.

7. Method as claimed in claim 6 wherein said PEI has been cross-linked in the presence of a primary straight-chained or branched alkylamine containing 3 to 12 carbon atoms.

8. Method as claimed in claim 1 wherein the anion exchanger is a cross-linked or non-cross-linked anion exchanger having a polymeric matrix containing bound dextrans.

9. Method as claimed in claim 8 wherein said bound dextrans have an average molecular weight of 200,000 to 800,000.

10. Method as claimed in claim 1 wherein a finely-divided porous carrier material is used and said material is coated or enveloped with the solid, water-insoluble anion exchanger.

11. Method as claimed in claim 10 wherein the finely-divided porous carrier material used is calcined clay, kieselguhr, diatomateous earth, glass with a definite pore size (CPG glasses) or a mixture of two or more of these carrier materials.

12. Method as claimed in claim 11 wherein the finely-divided porous carrier material used is CPG glass with an average pore diameter of 175 to 250 Å.

13. Method as claimed in claim 1 wherein said mixing of the blood plasma or serum with the anion exchanger comprises applying the plasma or serum to a column packed with the anion exchanger either alone or coated on a carrier and the step of separating the plasma or serum from the anion exchanger comprises eluting the column with various buffer solutions at a pH of from 6.5 to 7.5, to selectively elute the LDL, VLDL and HDL.

14. Method as claimed in claim 13 wherein the buffer solution used for the elution of the LDL is a sodium chlorideimidazole-hydrochloric acid buffer.

15. Method as claimed in claim 14 wherein after the elution of the LDL, the sodium chloride concentration of the buffer is increased stepwise until the VLDL can be detected in the elutate, the VLDL is then completely eluted at a constant sodium chloride concentration and thereafter the HDL is eluted with a pure aqueous sodium chloride solution.

16. Method as claimed in claim 1 wherein the anion exchanger used is a cross-linked or non-cross-linked basic ion exchanger, with quaternary ammonium groups as fixed ions.

17. Method as claimed in claim 16 wherein the anion exchanger used is a cross-linked polyethyleneimine (PEI).

18. Method as claimed in claim 16 wherein the anion exchanger used is a solid dextran containing quaternary ammonium groups as fixed ions.

19. Method as claimed in claim 18 wherein the anion exchanger used is a solid dextran containing diethyl-2-hydroxypropylammonium groups as fixed ions.

* * * * *

UNITED STATES PATENT AND TRADEMARK OFFICE
CERTIFICATE OF CORRECTION

PATENT NO. : 4,569,917
DATED : February 11, 1986
INVENTOR(S) : Josef Maier et al It is certified that error appears in the above-identified patent and that said Letters Patent are hereby corrected as shown below:

Col. 1, line 29, "liproproteins" should be -- lipoproteins --.
Col. 6, line 19 "presentn" should be -- present --.
Claim 1, col. 8, line 26, "liproprotein" should be
  -- lipoprotein --.
Claim 6, col. 8, lines 46 "claim 2" should be -- claim 1 --.

Signed and Sealed this

First Day of July 1986

[SEAL]

Attest:

DONALD J. QUIGG

Attesting Officer

Commissioner of Patents and Trademarks